(12) United States Patent
Shtirberg et al.

(10) Patent No.: US 10,672,510 B1
(45) Date of Patent: Jun. 2, 2020

(54) MEDICAL USER INTERFACE

(71) Applicant: Biosense Webster (Israel) Ltd., Yokneam (IL)

(72) Inventors: Illya Shtirberg, Nesher (IL); Assaf Cohen, Kiryat Bialik (IL); Gil Zigelman, Haifa (IL); Maxim Galkin, Haifa (IL); Ido Ilan, Yoqneam (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

(21) Appl. No.: 16/188,482

(22) Filed: Nov. 13, 2018

(51) Int. Cl.
| | | |
|---|---|---|
| *G06F 3/0482* | (2013.01) | |
| *G16H 30/40* | (2018.01) | |
| *G06F 3/0481* | (2013.01) | |
| *G06F 3/0484* | (2013.01) | |
| *A61B 18/14* | (2006.01) | |
| *A61B 34/00* | (2016.01) | |
| *A61B 90/00* | (2016.01) | |
| *A61B 18/00* | (2006.01) | |
| *A61M 25/01* | (2006.01) | |
| *A61B 34/10* | (2016.01) | |

(52) U.S. Cl.
CPC ......... *G16H 30/40* (2018.01); *A61B 18/1492* (2013.01); *A61B 34/25* (2016.02); *A61B 90/37* (2016.02); *G06F 3/0482* (2013.01); *G06F 3/04815* (2013.01); *G06F 3/04845* (2013.01); *A61B 2018/00577* (2013.01); *A61B 2018/00839* (2013.01); *A61B 2034/105* (2016.02); *A61B 2034/252* (2016.02); *A61B 2090/367* (2016.02); *A61B 2090/368* (2016.02); *A61M 2025/0166* (2013.01)

(58) Field of Classification Search
CPC .......... G06F 3/00; G06F 3/048; G06F 3/0481; G06F 3/0482; G06F 3/0484; G16H 30/40; G06K 9/00; G06T 15/00; A61B 5/04; A61B 5/05; A61B 8/00; A61B 18/14; A61B 34/00; A61B 90/00
See application file for complete search history.

(56) References Cited

U.S. PATENT DOCUMENTS

| | | |
|---|---|---|
| 6,226,542 B1 | 5/2001 | Reisfeld |
| 6,814,733 B2 | 11/2004 | Yitzhack Schwartz et al. |
| 6,892,091 B1 | 5/2005 | Ben-Haim et al. |
| 6,997,924 B2 | 2/2006 | Schwartz et al. |
| 7,156,816 B2 | 1/2007 | Schwartz et al. |

(Continued)

*Primary Examiner* — Xiomara L Bautista

(57) ABSTRACT

A system including a medical device to form a 3D image of an anatomical structure in a body of a living subject, a user interface including a display and an input device, and a processor to prepare a user interface screen presentation including a graphical representation of the anatomical structure based on the 3D image, generate a feature list of a plurality of features associated with the anatomical structure, each feature having a respective location, render the user interface screen presentation to the display showing a first view of the graphical representation, receive an input from the user interface selecting a feature from the list, and render the user interface screen presentation to the display showing the graphical representation of the anatomical structure being automatically rotated from the first view to a second view showing the selected feature at the respective location on the graphical representation.

30 Claims, 6 Drawing Sheets

(56) References Cited

U.S. PATENT DOCUMENTS

| | | | |
|---|---|---|---|
| 7,536,218 B2 | 5/2009 | Govari et al. | |
| 7,756,576 B2 | 7/2010 | Levin | |
| 2002/0105513 A1 | 8/2002 | Chen | |
| 2003/0152897 A1 | 8/2003 | Geiger | |
| 2009/0028403 A1 | 1/2009 | Bar-Aviv et al. | |
| 2010/0204816 A1* | 8/2010 | Sabiston | A61F 2/5046 700/98 |
| 2010/0299155 A1* | 11/2010 | Findlay | G06F 19/3418 705/3 |
| 2010/0316268 A1 | 12/2010 | Liang et al. | |
| 2012/0269407 A1* | 10/2012 | Criminisi | G06T 7/77 382/128 |
| 2013/0169640 A1* | 7/2013 | Sakuragi | G06T 15/20 345/424 |
| 2013/0325493 A1* | 12/2013 | Wong | G06F 19/00 705/2 |
| 2014/0122381 A1* | 5/2014 | Nowozin | G06N 20/00 706/12 |
| 2018/0344390 A1* | 12/2018 | Brannan | A61B 18/1477 |
| 2019/0056693 A1* | 2/2019 | Gelman | G02B 27/017 |

\* cited by examiner

MEDICAL USER INTERFACE

FIELD OF THE INVENTION

The present invention relates to a medical user interface, and in particular, to display of an image of a 3D anatomical structure in a medical user interface.

BACKGROUND

Medical images of various body parts may be formed in numerous ways for example but not limited to, X-ray radiography, magnetic resonance imaging (MRI), medical ultrasonography or ultrasound, endoscopy, elastography, tactile imaging, thermography, medical photography and nuclear medicine functional imaging techniques.

Volume rendering techniques have been developed to enable computed tomography (CT), MRI and ultrasound scanning software to produce three-dimensional (3D) images for the physician. Traditionally CT and MRI scans produced two-dimensional (2D) static output on film. To produce 3D images, many scans are made, then combined by computers to produce a 3D model, which can then be manipulated by the physician. 3D ultrasounds are produced using a somewhat similar technique.

US Patent Publication 2010/0316268 of Liang, et al., describes a procedure for pre-operating assessment of one or more anatomical structures generated from medical images and provided in a rendered 3D space, and an imaging system, apparatus, and computer program, that operate in accordance with the procedure. The procedure comprises providing one or more safety margin indicators in the rendered 3D space, each having a shape corresponding to that of a respective one of the anatomical structures within an organ and having a predetermined size of safety margin from the respective one of the anatomical structures. The procedure also comprises manipulating at least one of the shape and predetermined size of safety margin of at least one of the safety margin indicators in the rendered 3D space, and immediately providing a rendering in the 3D space of a manipulated version of the at least one safety margin indicator. Also provided is a procedure for defining at least one cutting surface to resect one or more medical anatomical structures using an imaging system.

US Patent Publication 2009/0028403 of Bar-Aviv, et al., describes a system for analyzing a source medical image of a body organ. The system comprises an input unit for obtaining the source medical image having three dimensions or more, a feature extraction unit that is designed for obtaining a number of features of the body organ from the source medical image, and a classification unit that is designed for estimating a priority level according to the features.

US Patent Publication 2003/0152897 of Geiger, describes a method for navigating a viewpoint of a virtual endoscope in a lumen of a structure. The method includes the steps of determining an initial viewpoint of the virtual endoscope, the initial viewpoint having a first center point and first direction, determining a longest ray from the initial viewpoint to the lumen, the longest ray having a first longest ray direction, determining a second direction between the first direction of the initial viewpoint and the first longest ray direction, turning the viewpoint to the second direction and moving the initial viewpoint a first predetermined distance in a first direction of the initial viewpoint, calculating a second center point of the viewpoint, moving the viewpoint to the second center point.

SUMMARY

There is provided in accordance with an embodiment of the present disclosure a system including a medical device configured to form a three-dimensional (3D) image of an anatomical structure in a body of a living subject, a user interface including a display and an input device, and a processor configured to prepare a user interface screen presentation including a graphical representation of the anatomical structure based on the 3D image, generate a feature list of a plurality of features associated with the anatomical structure, each of the features having a respective location, render the user interface screen presentation to the display showing a first view of the graphical representation of the anatomical structure, while showing the first view, receive an input from the user interface selecting a feature from the list, and render the user interface screen presentation to the display showing the graphical representation of the anatomical structure being automatically rotated from the first view to a second view showing the selected feature at the respective location on the graphical representation.

Further in accordance with an embodiment of the present disclosure the processor is configured to render the user interface screen presentation on the display showing the graphical representation of the anatomical structure being automatically rotated and automatically translated from the first view to the second view.

Still further in accordance with an embodiment of the present disclosure the processor is configured to render the user interface screen presentation on the display showing the graphical representation of the anatomical structure being automatically rotated and automatically translated from the first view to the second view so as to center the selected feature in a panel of the user interface screen presentation.

Additionally, in accordance with an embodiment of the present disclosure the processor is configured to render the user interface screen presentation on the display showing the graphical representation of the anatomical structure being automatically rotated from the first view to the second view and automatically zoomed in at the second view to enlarge the selected feature.

Moreover, in accordance with an embodiment of the present disclosure the processor is configured to generate at least part of the feature list from medical readings performed by the medical device with respect to at least some of the plurality of features.

Further in accordance with an embodiment of the present disclosure the medical readings include any one or more of the following a location of a catheter, at least one location of at least one electrode of the catheter, a location where an Electrocardiogram (ECG) had been performed, a location where an ablation has been performed, or a location where the ablation is planned to be performed.

Still further in accordance with an embodiment of the present disclosure, the system includes a probe including the plurality of electrodes and being configured to perform the ablation.

Additionally, in accordance with an embodiment of the present disclosure the processor is configured to receive an input from the user interface indicating addition of an annotation to the graphical representation at a respective location, the processor being configured to add the annotation to the feature list.

Moreover, in accordance with an embodiment of the present disclosure the annotation forms a perimeter of a shape.

Further in accordance with an embodiment of the present disclosure the processor is configured to render the user interface screen presentation on the display showing the graphical representation of the anatomical structure being automatically rotated and automatically translated from the first view to the second view so as to center the annotation based on a centroid of the shape of the annotation.

There is also provided in accordance with still another embodiment of the present disclosure a method including receiving a three-dimensional (3D) image of an anatomical structure in a body of a living subject, preparing a user interface screen presentation including a graphical representation of the anatomical structure based on the 3D image, generating a feature list of a plurality of features associated with the anatomical structure, each of the features having a respective location, rendering the user interface screen presentation to a display showing a first view of the graphical representation of the anatomical structure, while showing the first view, receiving an input from a user interface selecting a feature from the list, and rendering the user interface screen presentation to the display showing the graphical representation of the anatomical structure being automatically rotated from the first view to a second view showing the selected feature at the respective location on the graphical representation.

Still further in accordance with an embodiment of the present disclosure, the method includes rendering the user interface screen presentation on the display showing the graphical representation of the anatomical structure being automatically rotated and automatically translated from the first view to the second view.

Additionally, in accordance with an embodiment of the present disclosure, the method includes rendering the user interface screen presentation on the display showing the graphical representation of the anatomical structure being automatically rotated and automatically translated from the first view to the second view so as to center the selected feature in a panel of the user interface screen presentation.

Moreover, in accordance with an embodiment of the present disclosure, the method includes rendering the user interface screen presentation on the display showing the graphical representation of the anatomical structure being automatically rotated from the first view to the second view and automatically zoomed in at the second view to enlarge the selected feature.

Further in accordance with an embodiment of the present disclosure the generating includes generating at least part of the feature list from medical readings performed by a medical device with respect to at least some of the plurality of features.

Still further in accordance with an embodiment of the present disclosure the medical readings include any one or more of the following a location of a catheter, at least one location of at least one electrode of the catheter, a location where an Electrocardiogram (ECG) had been performed, a location where an ablation has been performed, or a location where the ablation is planned to be performed.

Additionally, in accordance with an embodiment of the present disclosure, the method includes performing the ablation.

Moreover, in accordance with an embodiment of the present disclosure, the method includes receiving an input from the user interface indicating addition of an annotation to the graphical representation at a respective location, and adding the annotation to the feature list.

Further in accordance with an embodiment of the present disclosure the annotation forms a perimeter of a shape.

Still further in accordance with an embodiment of the present disclosure, the method includes rendering the user interface screen presentation on the display showing the graphical representation of the anatomical structure being automatically rotated and automatically translated from the first view to the second view so as to center the annotation based on a centroid of the shape of the annotation.

There is also provided in accordance with still another embodiment of the present disclosure a system including a user interface including a display and an input device, and a processor configured to prepare a user interface screen presentation including a graphical representation of an anatomical structure based on a three-dimensional (3D) image of the anatomical structure in a body of a living subject, generate a feature list of a plurality of features associated with the anatomical structure, each of the features having a respective location, render the user interface screen presentation to the display showing a first view of the graphical representation of the anatomical structure, while showing the first view, receive an input from the user interface selecting a feature from the list, and render the user interface screen presentation to the display showing the graphical representation of the anatomical structure being automatically rotated from the first view to a second view showing the selected feature at the respective location on the graphical representation.

Additionally, in accordance with an embodiment of the present disclosure the processor is configured to render the user interface screen presentation on the display showing the graphical representation of the anatomical structure being automatically rotated and automatically translated from the first view to the second view.

Moreover, in accordance with an embodiment of the present disclosure the processor is configured to render the user interface screen presentation on the display showing the graphical representation of the anatomical structure being automatically rotated and automatically translated from the first view to the second view so as to center the selected feature in a panel of the user interface screen presentation.

Further in accordance with an embodiment of the present disclosure the processor is configured to render the user interface screen presentation on the display showing the graphical representation of the anatomical structure being automatically rotated from the first view to the second view and automatically zoomed in at the second view to enlarge the selected feature.

Still further in accordance with an embodiment of the present disclosure the processor is configured to generate at least part of the feature list from medical readings performed by a medical device with respect to at least some of the plurality of features.

Additionally, in accordance with an embodiment of the present disclosure the medical readings include any one or more of the following a location of a catheter, at least one location of at least one electrode of the catheter, a location where an Electrocardiogram (ECG) had been performed, a location where an ablation has been performed, or a location where the ablation is planned to be performed.

Moreover, in accordance with an embodiment of the present disclosure the processor is configured to receive an input from the user interface indicating addition of an annotation to the graphical representation at a respective location, the processor being configured to add the annotation to the feature list.

Further in accordance with an embodiment of the present disclosure the annotation forms a perimeter of a shape.

Still further in accordance with an embodiment of the present disclosure the processor is configured to render the user interface screen presentation on the display showing the graphical representation of the anatomical structure being automatically rotated and automatically translated from the first view to the second view so as to center the annotation based on a centroid of the shape of the annotation.

There is also provided in accordance with still another embodiment of the present disclosure a software product, including a non-transient computer-readable medium in which program instructions are stored, which instructions, when read by a central processing unit (CPU), cause the CPU to prepare a user interface screen presentation including a graphical representation of an anatomical structure based on a three-dimensional (3D) image of the anatomical structure in a body of a living subject, generate a feature list of a plurality of features associated with the anatomical structure, each of the features having a respective location, render the user interface screen presentation to a display showing a first view of the graphical representation of the anatomical structure, while showing the first view, receive an input from a user interface selecting a feature from the list, and render the user interface screen presentation to the display showing the graphical representation of the anatomical structure being automatically rotated from the first view to a second view showing the selected feature at the respective location on the graphical representation.

BRIEF DESCRIPTION OF THE DRAWINGS

The present invention will be understood from the following detailed description, taken in conjunction with the drawings in which.

DESCRIPTION OF EXAMPLE EMBODIMENTS

Overview

Figure 1:
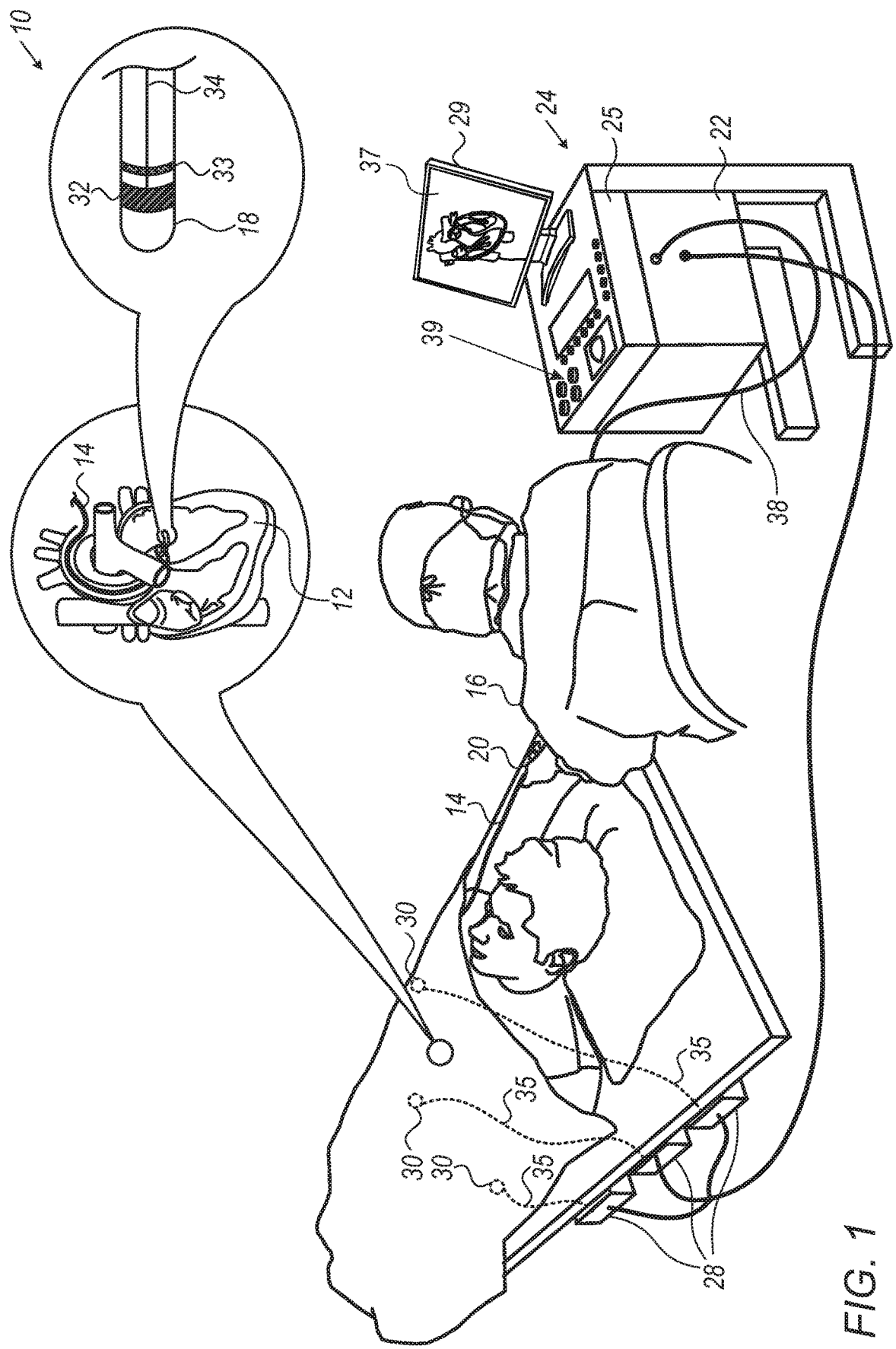
FIG. 1 is a partly pictorial, partly block diagram view of a medical imaging system constructed and operative in accordance with an embodiment of the present invention.

In attempting to present a three-dimensional (3D) image of a body-part, such as a heart chamber, on a two-dimensional (2D) screen, it is often difficult to locate a specific item of the 3D image, without manual rotation by means of a user interface and visual inspection of the image by the user. This may be time consuming and could result in identifying the incorrect item or identifying the correct item too late. In some cases, medical mistakes could be made, and in the middle of a medical procedure such a mistake could be critical where making timely and correct decisions may be essential to the success of the medical procedure.

Embodiments of the present invention provide a system including a user interface screen presentation which allows a user to select features of an anatomical structure from a list of features (or feature list) even though the selected feature may not currently be in view. A graphical representation of the anatomical structure is automatically rotated by the system until the selected feature is shown to the user on the screen. In order for the user to see the context of the position of the selected feature with respect to other features of the anatomical structure, the system shows the anatomical structure being rotated until the selected feature is shown. In the above manner, even features hidden from view may be found both quickly and accurately thereby reducing the human error factor.

As the anatomical structure is generally not spherical, simply rotating the graphical representation may result in the selected feature being displayed in a less than optimal fashion. Therefore, in some embodiments, the system also automatically translates (shifts) the graphical representation to display the selected feature in a more optimal fashion, for example, but not limited to, in the center of a display panel on the screen. In order for the user to see the context of the position of the selected feature, the system shows the anatomical structure being translated (shifted) on the screen.

In some embodiments, the system may also zoom-in to the selected feature so that the selected feature may be viewed with greater ease and in order for the user to see the context of the position of the selected feature. The system can thus show the anatomical structure being enlarged on the screen.

The graphical representation of the anatomical structure is generally derived from a 3D image of the anatomical structure which is formed by a medical device. The medical device may take medical readings described in more detail below. Such a medical device may comprise a non-invasive device, such as a CT or MRI scanner, for example, or an invasive device, such as a catheter that is inserted into and maps the anatomical structure. The term "3D image," as used in the context of the present description and in the claims, encompasses all such types of 3D data, including, without limitation, 3D scans and 3D maps of anatomical structures.

The feature list includes features associated with the anatomical structure with each feature having a respective location with respect to the graphical representation of the anatomical structure. The features may be generated automatically and/or manually.

Automatic generation of the feature list may be performed by the system based on medical readings of the medical device, for example, but not limited to, a location of a catheter, a location(s) of an electrode(s) of the catheter, a location where an Electrocardiogram (ECG) had been performed, a location where an ablation has been performed, or a location where the ablation is planned to be performed. The feature list may include a general description of the feature, e.g., catheter location X, ablation point Y, or planned ablation Z. The feature list may also include more detailed information, for example, but not limited to, detailed position coordinates, electrical readings, ablation timings or temperatures.

Additionally, or alternatively, the feature list may be generated by the user adding annotations to the graphical representation at various respective locations on the graphical representation of the anatomical structure. The annotations may comprise icons, shapes or even free-form annotations. The user may add suitable descriptive text to each annotation which is added to the feature list to enable easy user selection of the added annotation.

System Description

Documents incorporated by reference herein are to be considered an integral part of the application except that, to the extent that any terms are defined in these incorporated documents in a manner that conflicts with definitions made explicitly or implicitly in the present specification, only the definitions in the present specification should be considered.

Turning now to the drawings, reference is initially made to FIG. 1, which is a partly pictorial, partly block diagram view of a medical imaging system 10 constructed and operative in accordance with an embodiment of the present invention. The medical imaging system 10 includes a medical device to form a three-dimensional (3D) image of an anatomical structure in a body of a living subject. The anatomical structure may be any suitable anatomical structure, for example, but not limited to a limb or part thereof, an internal organ or any other suitable body part. In the example of FIGS. 1-10, a heart 12 is shown as the anatomical structure used to illustrate some embodiments of the present invention. The 3D image of the anatomical structure is used as input to a user interface screen presentation, which is described in more detail with reference to FIGS. 2-11. The 3D image may be formed using the system and method described herein below with reference to FIG. 1 where the 3D image of the anatomical structure (e.g., the heart 12) may be formed using mapping techniques based on positions of a probe 14. Additionally, or alternatively, the 3D scan may be formed using any suitable medical imaging method including ultrasound, Magnetic Resonance Imaging (MRI), or computed tomography (CT) scans by way of example only.

The system 10 comprises the probe 14, such as a catheter, which is percutaneously inserted by an operator 16 through the patient's vascular system into a chamber or vascular structure of the heart 12. The operator 16, who is typically a physician, brings a distal tip 18 of the probe 14 into contact with the heart wall, for example, at an ablation target site to perform an ablation or to capture electrical potentials over time at multiple sample locations over a surface of one or more chambers of the heart 12 or to capture positions of the surface of the heart 12 in order to generate the 3D image of the heart. Electrical activation maps may be prepared, according to the methods disclosed in U.S. Pat. Nos. 6,226,542, and 6,301,496, and in commonly assigned U.S. Pat. No. 6,892,091, whose disclosures are herein incorporated by reference. One commercial product embodying elements of the system 10 is available as the CARTO® 3 System, available from Biosense Webster, Inc., 33 Technology Drive, Irvine, Calif. 92618 USA. This system may be modified by those skilled in the art to embody the principles of the invention described herein.

Areas determined to be abnormal, for example by evaluation of the electrical activation maps, can be ablated by application of thermal energy, e.g., by passage of radiofrequency electrical current through wires in the probe 14 to one or more electrodes at the distal tip 18, which apply the radiofrequency energy to the myocardium. The energy is absorbed in the tissue, heating it to a temperature (typically about 50° C.) at which it permanently loses its electrical excitability. When successful, this procedure creates non-conducting lesions in the cardiac tissue, which disrupt the abnormal electrical pathway causing the arrhythmia. The principles of the invention can be applied to different heart chambers to diagnose and treat many different cardiac arrhythmias.

The probe 14 typically comprises a handle 20, having suitable controls on the handle to enable the operator 16 to steer, position and orient the distal tip 18 of the probe 14 as desired for the ablation. To aid the operator 16, a distal portion of the probe 14 contains position sensors (not shown) that provide signals to a processor 22, located in a console 24. The processor 22 may fulfill several processing functions as described below.

Ablation energy and electrical signals can be conveyed to and from the heart 12 through one or more ablation electrodes 32 located at or near the distal tip 18 of the probe 14 via cable 34 to the console 24. In such a manner, the ablation electrodes 32 of the probe 14 are configured to capture electrical potentials over time at multiple sample locations over a surface of one or more chambers of the heart 12. Additionally, or alternatively, other electrodes may be configured to capture electrical potentials over time at multiple sample locations over a surface of one or more chambers of the heart 12. Pacing signals and other control signals may be conveyed from the console 24 through the cable 34 and the electrodes 32 to the heart 12. Sensing electrodes 33, also connected to the console 24 are disposed between the ablation electrodes 32 and have connections to the cable 34. The probe 14 may be implemented without the ablation electrodes 32 as an exploratory device having electrodes configured to capture electrical potentials over time at multiple sample location over a surface of one or more chambers of the heart 12.

Wire connections 35 link the console 24 with body surface electrodes 30 and other components of a positioning sub-system for measuring location and orientation coordinates of the probe 14. The processor 22 or another processor (not shown) may be an element of the positioning subsystem. The electrodes 32 and the body surface electrodes 30 may be used to measure tissue impedance at the ablation site as taught in U.S. Pat. No. 7,536,218, issued to Govari et al., which is herein incorporated by reference. A sensor for bioelectric information, e.g., a temperature sensor (not shown), typically a thermocouple or thermistor, may be mounted on or near each of the electrodes 32.

The console 24 typically contains one or more ablation power generators 25. The probe 14 may be adapted to conduct ablative energy to the heart using any known ablation technique, e.g., radiofrequency energy, ultrasound energy, and laser-produced light energy. Such methods are disclosed in commonly assigned U.S. Pat. Nos. 6,814,733, 6,997,924, and 7,156,816, which are herein incorporated by reference.

In one embodiment, the positioning subsystem comprises a magnetic position tracking arrangement that determines the position and orientation of the probe 14 by generating magnetic fields in a predefined working volume and sensing these fields at the probe 14, using field generating coils 28. The positioning subsystem is described in U.S. Pat. No. 7,756,576, which is hereby incorporated by reference, and in the above-noted U.S. Pat. No. 7,536,218.

As noted above, the probe 14 is coupled to the console 24, which enables the operator 16 to observe and regulate the functions of the probe 14. The processor 22 may be embodied as a computer with appropriate signal processing circuits. The processor 22 is coupled to drive a monitor 29 including a display 37. The signal processing circuits typically receive, amplify, filter and digitize signals from the probe 14, including signals generated by sensors such as electrical, temperature and contact force sensors, and a plurality of location sensing electrodes (not shown) located distally in the probe 14. The digitized signals are received and used by the console 24 and the positioning system to compute the position and orientation of the probe 14, and to analyze the electrical signals from the electrodes.

In order to generate electroanatomic maps, the processor 22 typically comprises an electroanatomic map generator, an image registration program, an image or data analysis program and a graphical user interface configured to present graphical information on the monitor 29.

In practice, some or all of these functions of the processor 22 may be combined in a single physical component or, alternatively, implemented using multiple physical components. These physical components may comprise hard-wired or programmable devices, or a combination of the two. In some embodiments, at least some of the functions of the processor may be carried out by a programmable processor under the control of suitable software. This software may be downloaded to a device in electronic form, over a network, for example. Alternatively or additionally, the software may be stored in tangible, non-transitory computer-readable storage media, such as optical, magnetic, or electronic memory.

The console 24 may also include a user interface comprising the display 37 and an input device 39 to receive input commands from the operator 16 (or other user) via any suitable user input device, for example, but not limited to, a pointing device (such as a mouse of stylus), a keyboard, and/or a touch sensitive screen implemented in the display 37.

Typically, the system 10 includes other elements, which are not shown in the figures for the sake of simplicity. For example, the system 10 may include an electrocardiogram (ECG) monitor, coupled to receive signals from the body surface electrodes 30, in order to provide an ECG synchronization signal to the console 24. As mentioned above, the system 10 typically also includes a reference position sensor, either on an externally applied reference patch attached to the exterior of the subject's body, or on an internally placed probe, which is inserted into the heart 12 maintained in a fixed position relative to the heart 12. Conventional pumps and lines for circulating liquids through the probe 14 for cooling the ablation site are provided. The system 10 may receive image data from an external imaging modality, such as an MRI unit or the like and includes image processors that can be incorporated in or invoked by the processor 22 for generating and displaying images.

Figure 2:
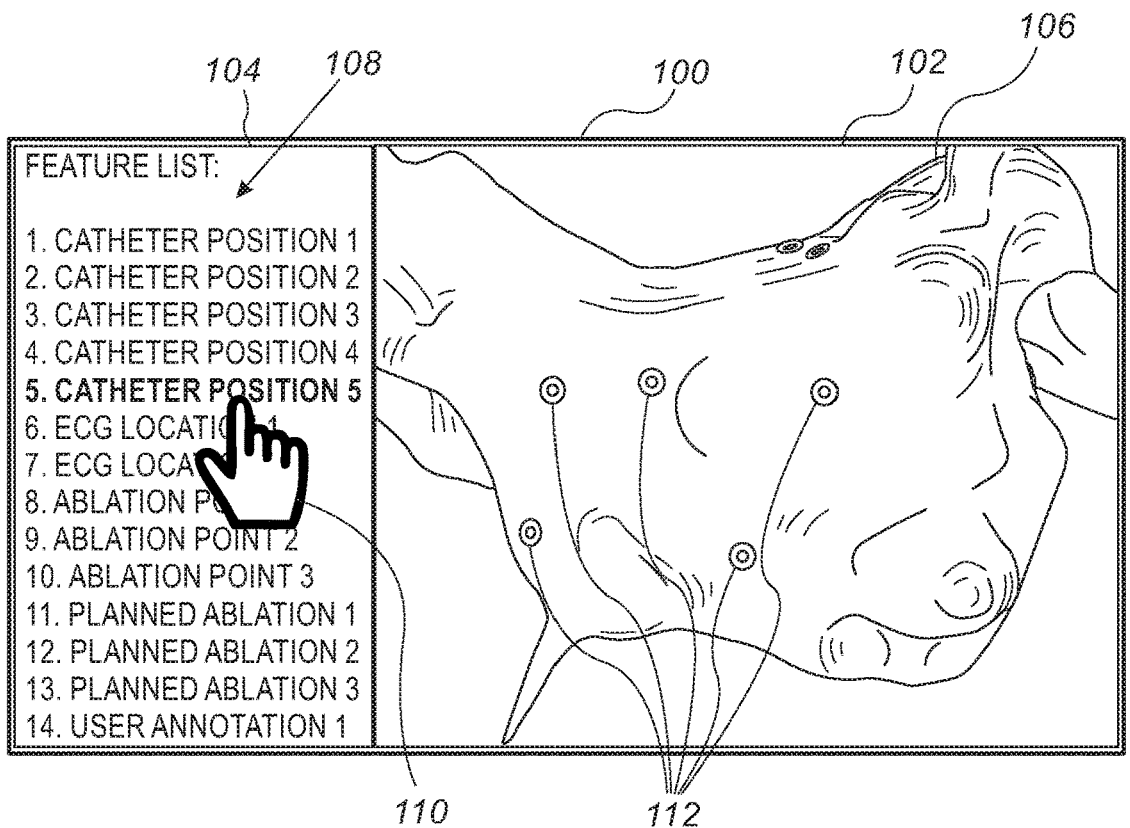
FIG. 2 is a schematic view of a user interface screen presentation for use with the medical imaging system of FIG. 1.
Figure 3:
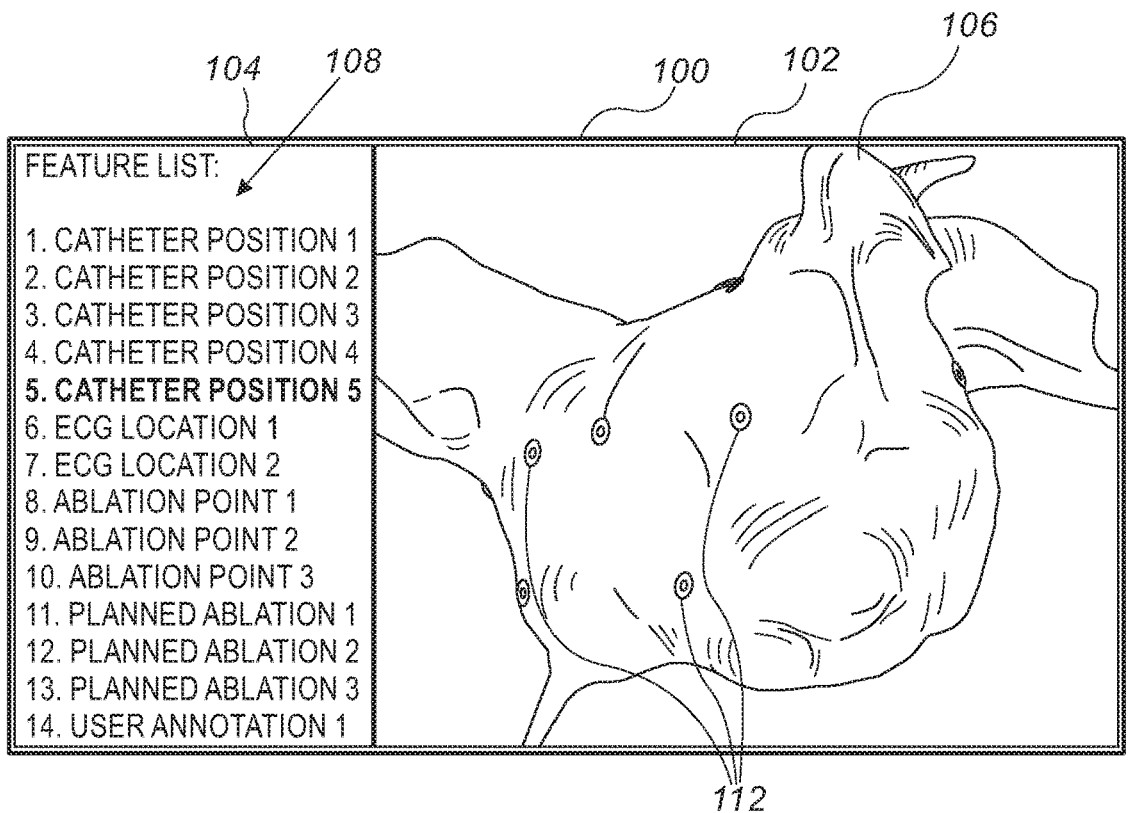
FIGS. 3-9 are schematic views of the user interface screen presentation of FIG. 2 illustrating rotation, translation, and zooming to a selected feature.
Figure 4:
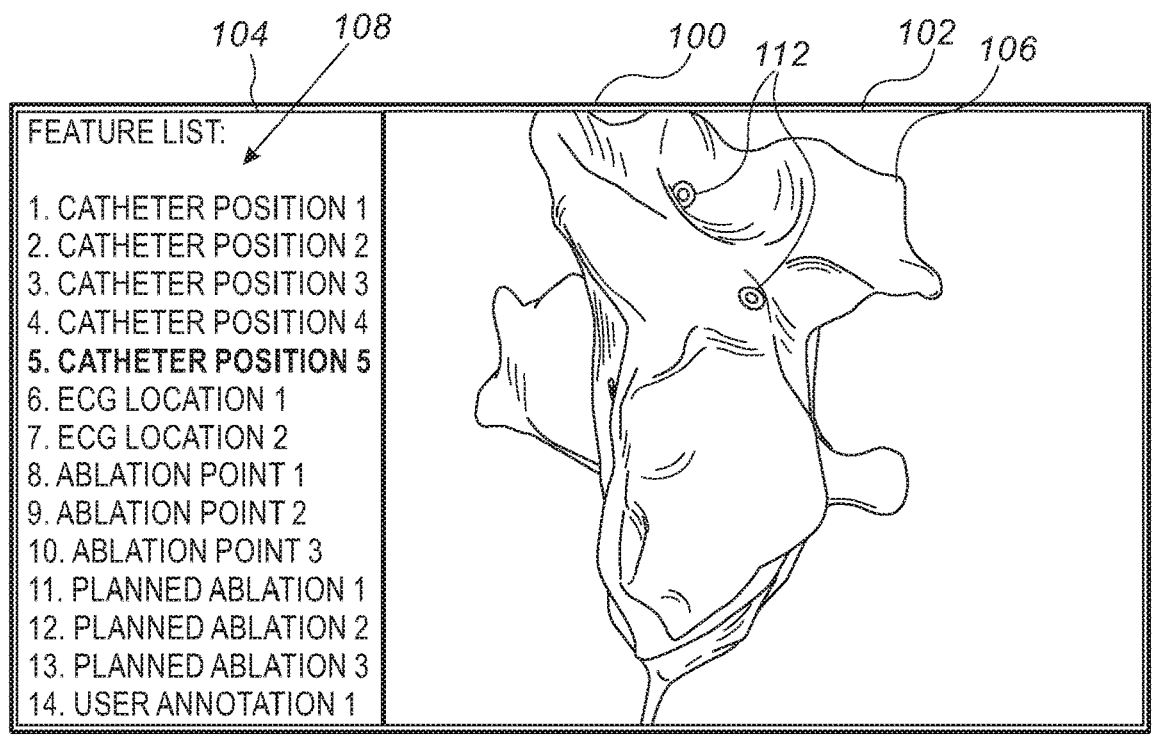
Figure 5:
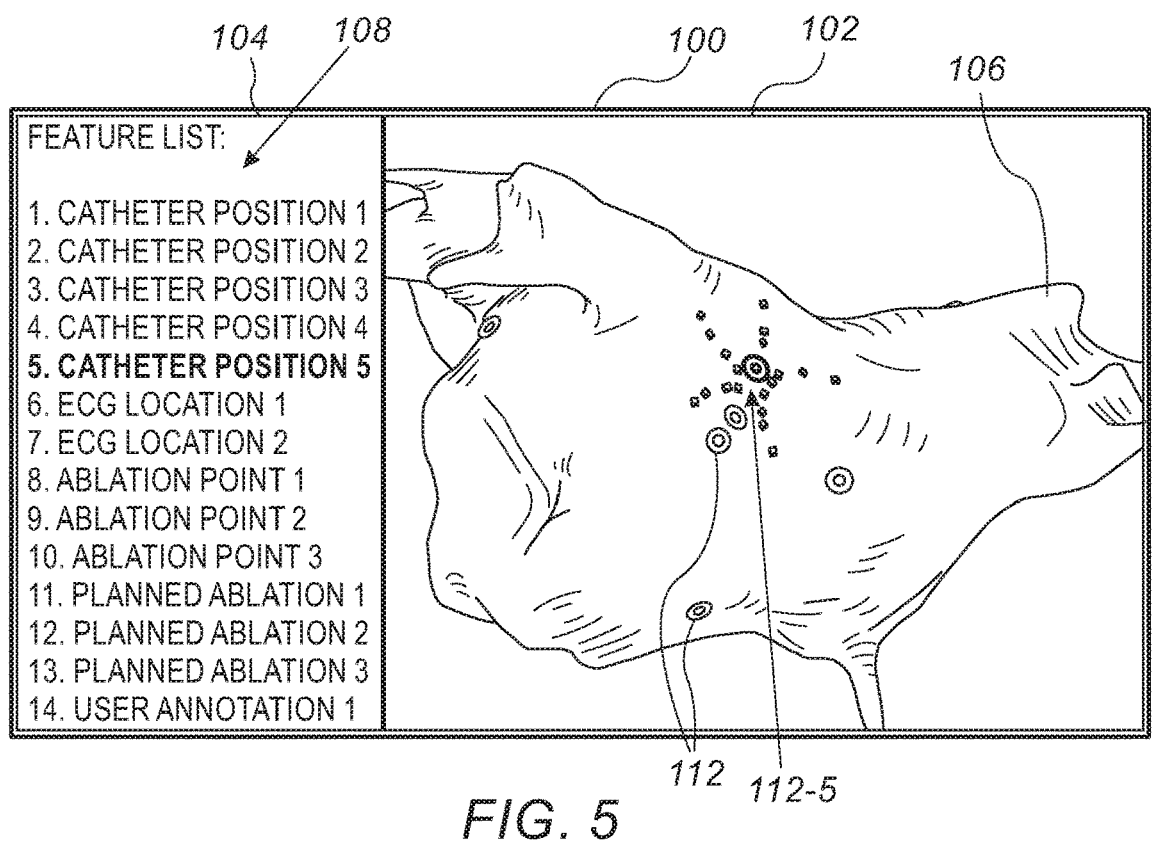

Reference is now made to FIG. 2, which is a schematic view of a user interface screen presentation 100 for use with the medical imaging system 10 of FIG. 1. The user interface screen presentation 100 includes an image panel 102 and a feature list panel 104. The image panel 102 includes one view of a graphical representation 106 of an anatomical structure (e.g., the heart 12 (FIG. 1) or any other suitable body part). The graphical representation 106 is derived from a three-dimensional (3D) image of the anatomical structure formed by the medical imaging system 10 or any suitable imaging device. The graphical representation 106 includes a plurality of features 112 which may represent various features associated with the anatomical structure, such as a prior catheter position, a current catheter position, an ECG location, an ablation point, a planned ablation point or any other suitable feature. The features 112 shown in FIG. 2 have been shown as annuli (2D donut shapes). The features 112 may be represented by any suitable shape and/or format (e.g., color and/or shading). Different types of features 112 may be shown using different shapes and/or different formats. For the sake of simplicity all the features 112 include an identical symbol. In the figures, only some of the features 112 have been labeled for the sake of simplicity.

The feature list panel 104 includes a feature list 108 listing the various features 112 of the anatomical structure. Each feature 112 has a respective location on the graphical representation 106 which may be derived from the 3D image or based on a location on the graphical representation 106 at which the feature 112 was added. Some of the features 112 are shown on the current view of the graphical representation 106 as shown in FIG. 2 whereas other features 112 may be currently hidden from view as the features 112 are disposed on a side of the graphical representation 106 which is not shown in FIG. 2. While the user interface screen presentation 100 is still showing the current view of the graphical representation 106, a user may select one of the features 112 from the feature list 108. FIG. 2 illustrates a cursor 110, manipulated by the user, hovering of item 5 in the feature list 108. The user then performs a selection action to select display of item 5 from the feature list 108. The processor 22 (FIG. 1) is configured to receive an input from the input device 39 of the user interface selecting the feature (e.g., item 5) from the feature list 108. Item 5 is not included in the current view of the graphical representation 106, therefore the graphical representation 106 is rotated to show item 5 as will be described below with reference to FIGS. 3-6.

Reference is now made to FIGS. 3-9, which are schematic views of the user interface screen presentation 100 of FIG. 2 illustrating rotation, translation, and zooming to a selected feature. FIGS. 3-6 show the graphical representation 106 being gradually automatically rotated from the view shown in FIG. 2 to a new view shown in FIG. 6, which includes the selected item 5, feature 112-5. The feature 112-5 is first shown in FIG. 5.

Figure 6:
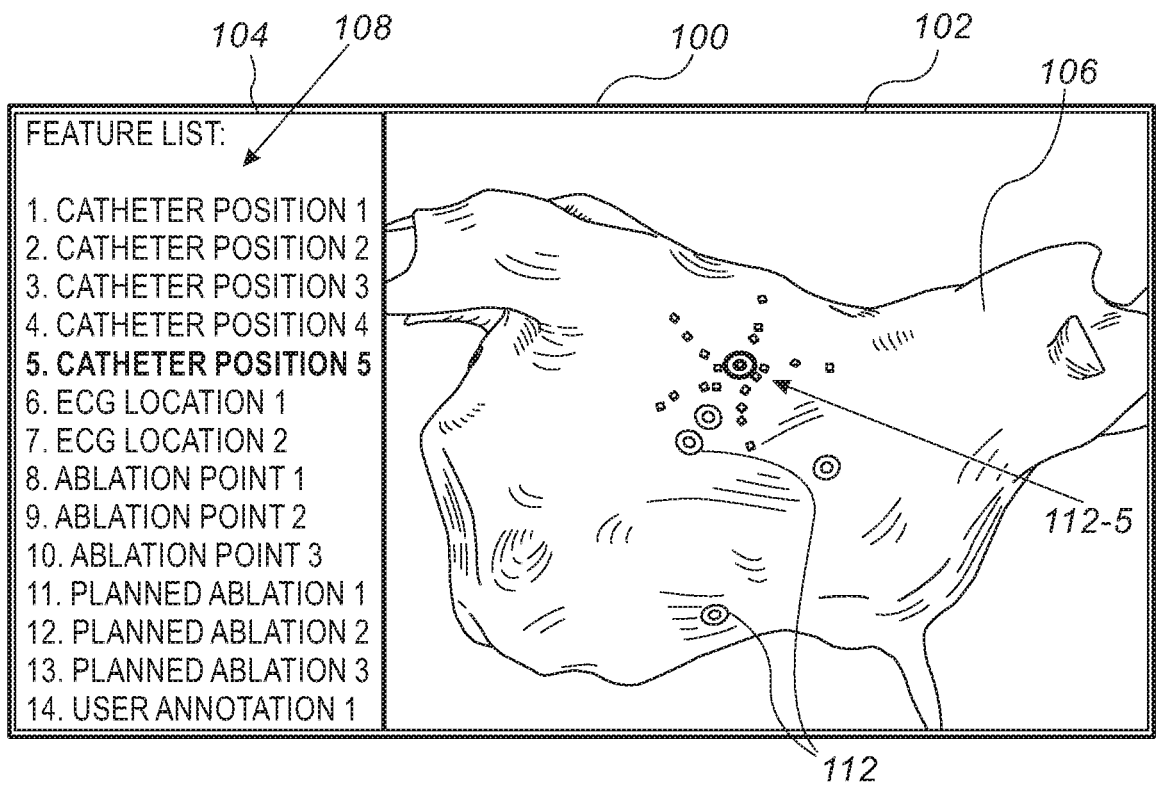

The feature 112-5 includes an annulus which is surrounded by a ring to indicate that it is the selected feature 112. FIG. 6 also shows squares (not labeled) that are generally disposed on lines extending outward from the annulus. The squares represent electrode positions of the catheter when the catheter was at position 5.

Figure 7:
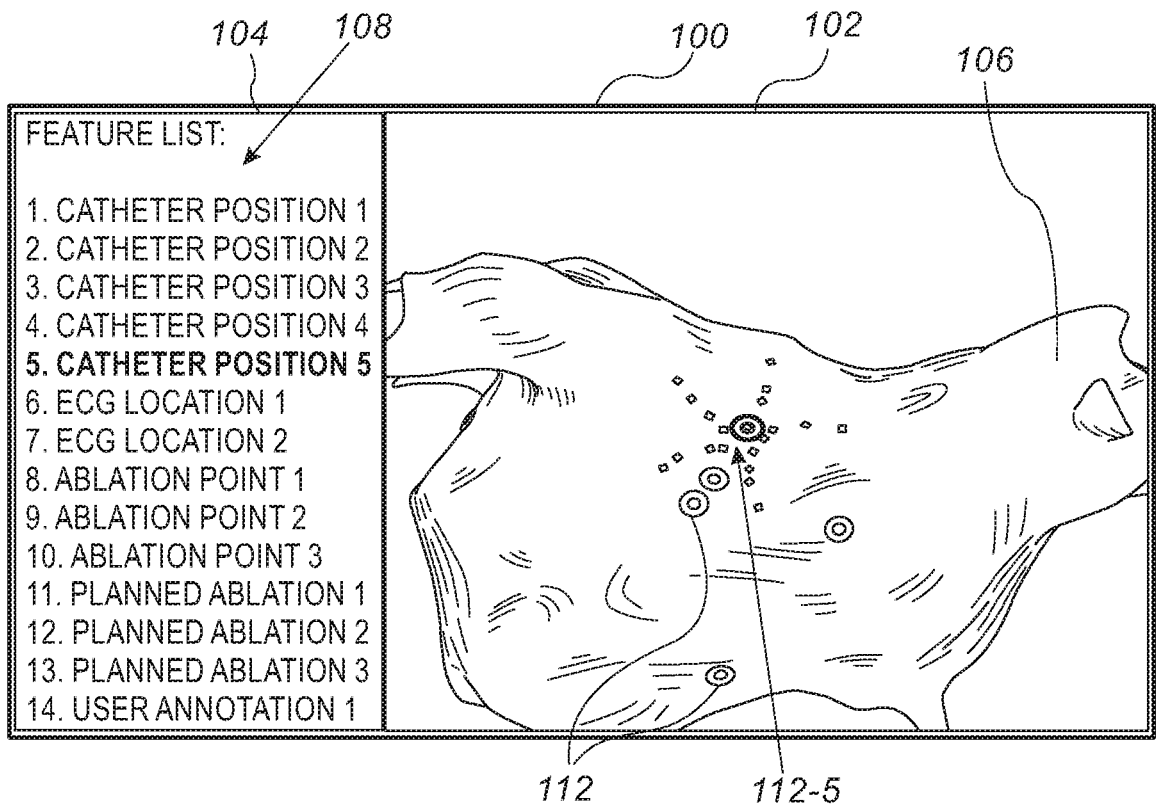

The selected feature 112-5 is still not centered in the image panel 102. Therefore, in some embodiments, the processor 22 automatically translates (shifts) the graphical representation 106 (e.g., up, down, left and/or right or any suitable combination thereof) so that the selected feature 112-5 is shown in the center of the image panel 102 as shown in FIG. 7. The center of the feature 112-5 may be defined by a center of the annulus of the feature 112-5 or by a centroid of a shape encompassing the annulus and the squares representing the electrode positions.

In some embodiments, because the graphical representation 106 is non-spherical, while the graphical representation 106 is being automatically rotated from one view to another, the graphical representation 106 may also be automatically translated (shifted) (e.g., up, down, left and/or right or any suitable combination thereof) any number of times to keep whatever side of the graphical representation 106 is being shown in view and generally centrally positioned in the image panel 102. In some embodiments the user has the ability to manually rotate and translate the graphical representation 106 within the image panel 102.

In some embodiments, in order to provide a better view of the selected feature 112-5, the graphical representation 106 is automatically rotated and/or translated so that a plane of the feature 112-5 is parallel with the plane of the image panel 102. The plane of the feature 112-5 may be defined as a plane defining average positions of the various points, for example, using a least square fit of the points of the feature 112-5.

Figure 8:
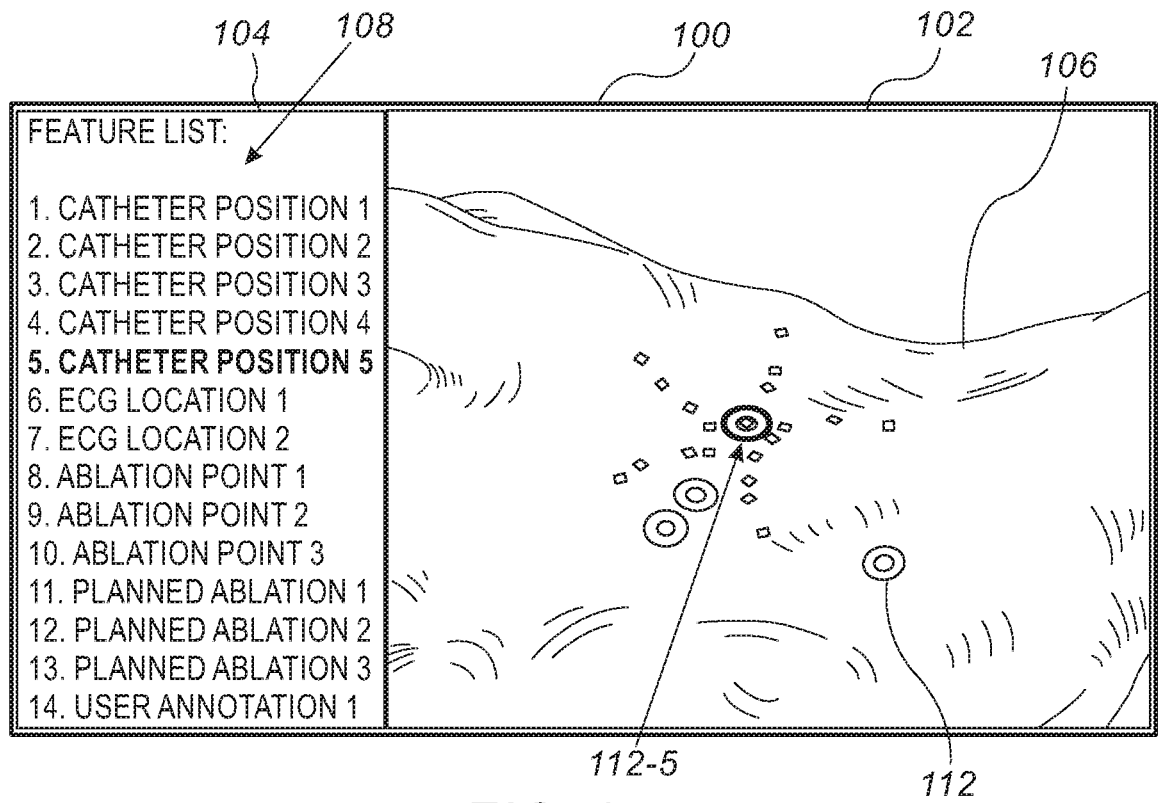
Figure 9:
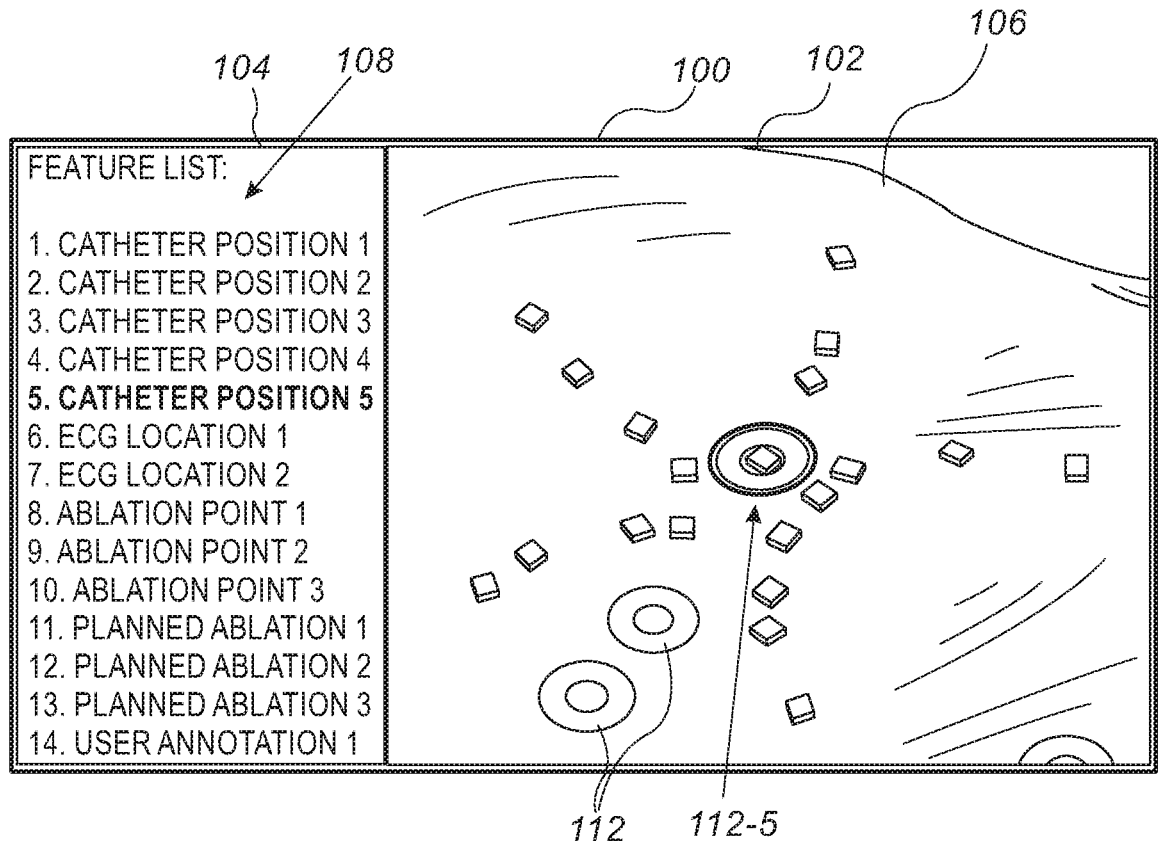

FIGS. 8-9 show the graphical representation 106 being enlarged (zoomed-in) thereby enlarging the view of the feature 112-5. If another feature 112 is selected from the feature list 108, the processor 22 is configured to zoom-out of the view of the graphical representation 106 prior to rotating the graphical representation 106 to the new view of the graphical representation 106. In some embodiments, the graphical representation 106 may not be scaled down or up.

The rotation, translation, and scaling of the graphical representation 106 may be performed using a suitable function, for example, but not limited to, an affine transformation.

Figure 10:
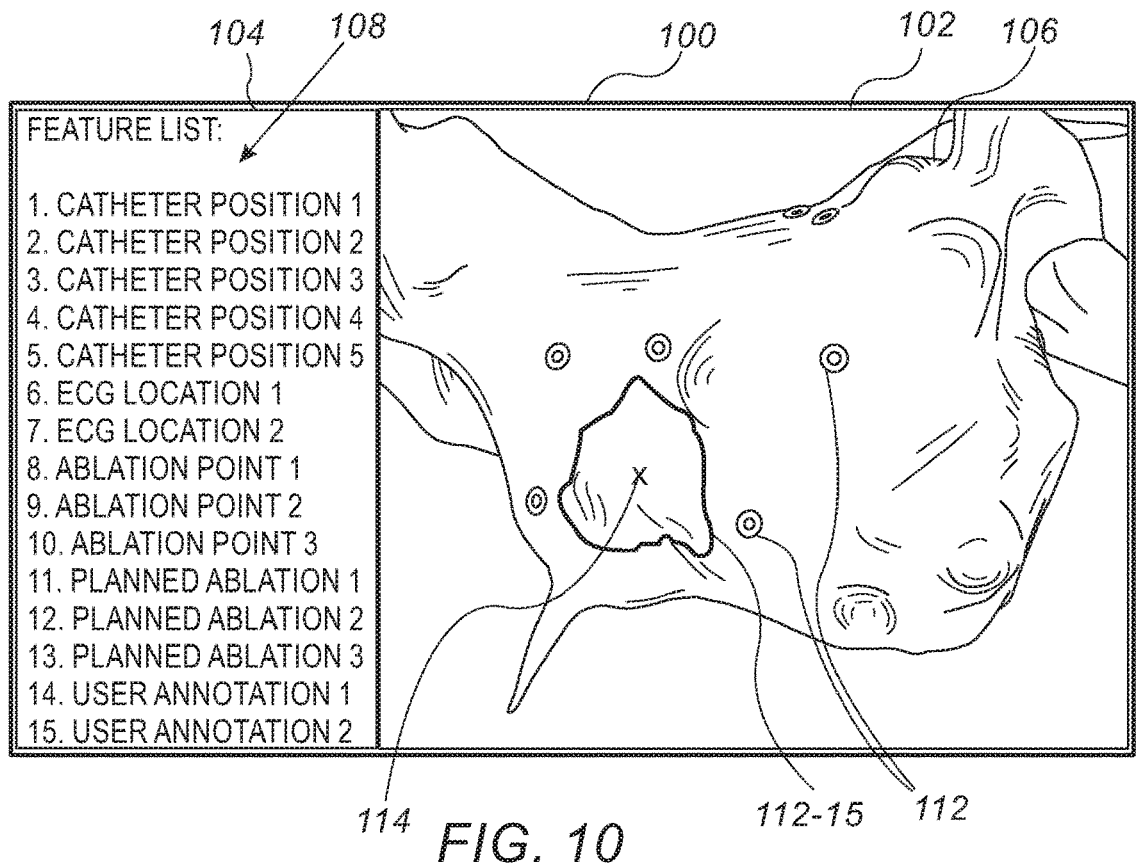
FIG. 10 is a schematic view of the user interface screen presentation of FIG. 2 illustrating addition of an annotation.

Reference is now made to FIG. 10, which is a schematic view of the user interface screen presentation 100 of FIG. 2 illustrating addition of an annotation 112-15. The processor 22 (FIG. 1) is configured to receive an input from the input device 39 of the user interface indicating addition of the annotation 112-15 to the graphical representation 106 at a respective location. The annotation 112-15 forms a perimeter of a shape. The shape shown in FIG. 10 is an irregular shape formed by a user drawing a line on the graphical representation 106 using a suitable pointing device such as a mouse or stylus. The shape may be any suitable shape including a regular shape such as a rectangle, square, ellipse, circle, or triangle, by way of example only. In some embodiments, the annotation may include a symbol, graphic, and/or picture. The processor 22 is configured to add the annotation 112-15 to the feature list 108. In the example of FIG. 10, the annotation 112-5 is added as item 15 in the feature list 108.

If the newly added feature 112-15 is selected by the user from the feature list 108, the processor 22 is configured to render the user interface screen presentation 100 showing the graphical representation 106 of the anatomical structure being automatically rotated (and optionally automatically translated and/or zoomed) from a current view to another view of the graphical representation 106 so as to center the annotation 112-15 based on a centroid 114 of the shape of the annotation 112-15.

Figure 11:
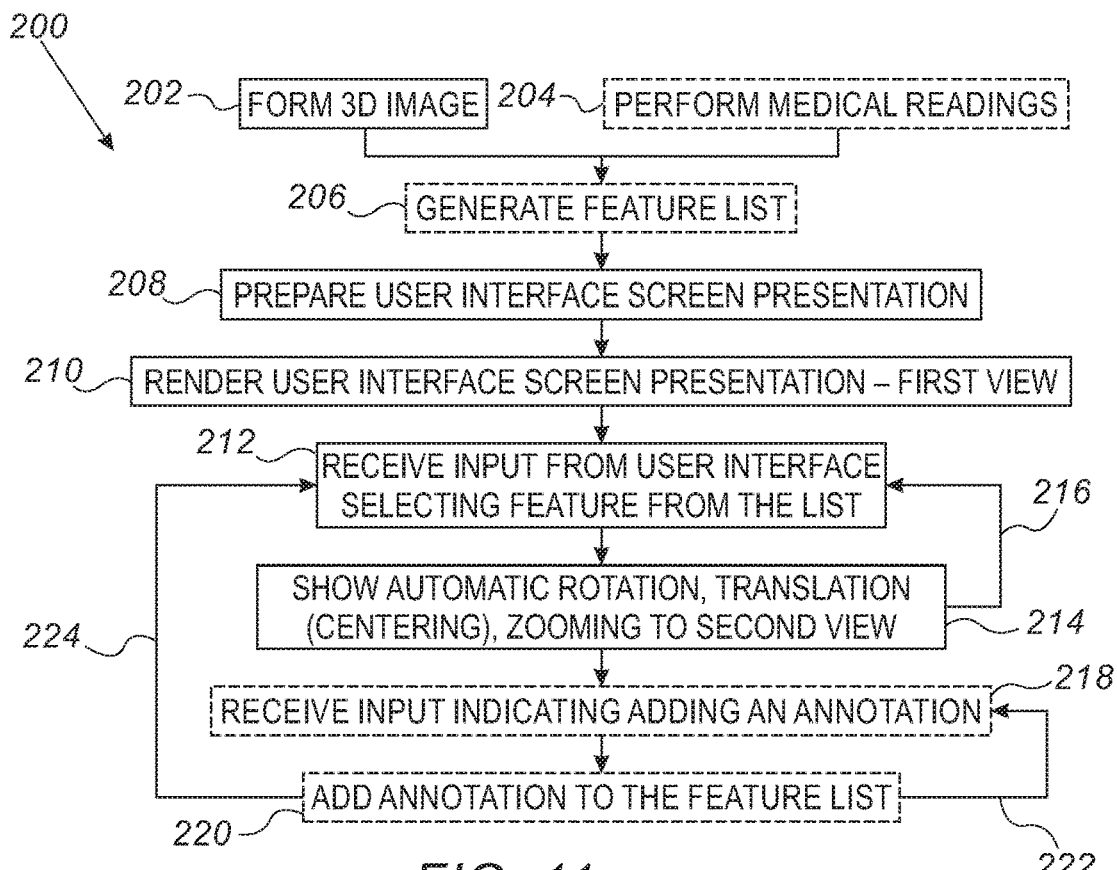
FIG. 11 is a flow chart including exemplary steps in a method of operation of the medical imaging system of FIG. 1.

Reference is now made to FIG. 11, which is a flow chart 200 including exemplary steps in a method of operation of the medical imaging system 10 of FIG. 1. A medical device (such as one included in the medical imaging system 10) is configured to form (block 202) (e.g., by scanning or mapping data) the 3D image of the anatomical structure in the body of the living subject. In some embodiments, the medical device is configured to perform medical readings (block 204) using a suitable device, for example, but not limited to, using the probe 14 (FIG. 1). The medical readings may include any one or more of the following, by way of example only: a (current or previous) location of a catheter, at least one location of at least one electrode of the catheter, a location where an ECG had been performed, a location where an ablation has been performed, or a location where an ablation is planned to be performed.

The processor 22 is configured to generate (block 206) the feature list 108 (FIGS. 2-10) of the features 112 associated with the anatomical structure. Each feature 112 has a respective location with respect to the graphical representation 106 of the anatomical structure and/or the 3D scan. In some embodiments, the processor 22 is configured to generate at least part of the feature list 108 from medical readings performed by the medical device with respect to at least some of the features 112. In some embodiments, the feature list 108 is generated based on user generated annotations described with reference to steps of blocks 218-220 below.

The processor 22 is configured to prepare (block 208) the user interface screen presentation 100 (FIGS. 2-10) including the graphical representation 106 (FIGS. 2-10) of the anatomical structure based on the 3D image. The processor 22 is configured to render (block 210) the user interface screen presentation 100 to the display 37 (FIG. 1) showing a first view of the graphical representation 106 of the anatomical structure. While showing the first view, the processor 22 is configured to receive (block 212) an input from the input device 39 of the user interface selecting one of the features 112 from the feature list 108.

The processor 22 is configured to render the user interface screen presentation 100 to the display 37 showing (block 214) the graphical representation 106 of the anatomical structure being automatically rotated from the first view to a second view, which shows the selected feature 112 at the respective location on the graphical representation 106. In some embodiments, the processor 22 is configured to render the user interface screen presentation 100 on the display 37 showing the graphical representation 106 of the anatomical structure being automatically rotated and automatically translated from the first view to the second view. In some embodiments, the processor 22 is configured to render the user interface screen presentation 100 on the display 37 showing the graphical representation 106 of the anatomical structure being automatically rotated and automatically translated from the first view to the second view so as to center (horizontally and/or vertically) the selected feature 112 in the image panel 102 (FIGS. 2-10) of the user interface screen presentation 100. In some embodiments, the processor 22 is configured to render the user interface screen presentation 100 on the display 37 showing the graphical representation 106 of the anatomical structure being automatically rotated (and translated) from the first view to the second view and automatically zoomed in at the second view to enlarge the selected feature 112. The steps of blocks 212 and 214 may be repeated (arrow 216) based on newly selected features 112 selected by the user.

In some embodiments, the processor 22 is configured to receive (block 218) an input from the input device 39 of the user interface indicating addition of an annotation to the graphical representation 106 at a respective location. The annotation forms a perimeter of a shape. The shape may be an irregular shape, for example, formed by a user drawing a line on the graphical representation 106 using a suitable pointing device such as a mouse or stylus. The shape may be any suitable shape including a regular shape such as a rectangle, square, ellipse, circle, or triangle, by way of example only. Additionally, or alternatively, the annotation may include a symbol, graphic, and/or picture. The processor 22 is configured to add (block 220) the annotation to the feature list 108. More annotations may be added to the list by repeating (arrow 222) the steps of blocks 218-220.

Additional features 112 may be selected by the user from the feature list 108 leading to the graphical representation 106 automatically rotating (and optionally translating and/or zooming) in the image panel 102 to the selected features 112 by repeating (arrow 224) the steps of blocks 212-214. One of the selected features 112 may include a user added annotation. In such a case, the processor 22 is configured to render the user interface screen presentation 100 on the display 37 showing the graphical representation 106 of the anatomical structure being automatically rotated (and optionally automatically translated and/or automatically zoomed) from a current view to another view including the selected annotation. In some embodiments, the processor 22 is configured to render the user interface screen presentation 100 on the display 37 showing the graphical representation 106 of the anatomical structure being automatically rotated and automatically translated (and optionally automatically zoomed) from a current view to another view so as to center the selected annotation based on the centroid 114 of the shape of the annotation.

Various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination.

The embodiments described above are cited by way of example, and the present invention is not limited by what has been particularly shown and described hereinabove. Rather the scope of the invention includes both combinations and subcombinations of the various features described hereinabove, as well as variations and modifications thereof which would occur to persons skilled in the art upon reading the foregoing description and which are not disclosed in the prior art.

What is claimed is:

1. A system comprising:
   a medical device configured to form a three-dimensional (3D) image of an anatomical structure in a body of a living subject;
   a user interface comprising a display and an input device; and
   a processor configured to:
      prepare a user interface screen presentation including a graphical representation of the anatomical structure based on the 3D image;
      generate a feature list of a plurality of features associated with the anatomical structure, each of the features having a respective location;
      render the user interface screen presentation to the display showing a first view of the graphical representation of the anatomical structure;
      while showing the first view, receive an input from the user interface selecting a feature from the list; and
      render the user interface screen presentation to the display showing the graphical representation of the anatomical structure being automatically rotated from the first view to a second view showing the selected feature at the respective location on the graphical representation, including showing the anatomical structure as it is being rotated until the selected feature is shown.

2. The system according to claim 1, wherein the processor is configured to render the user interface screen presentation on the display showing the graphical representation of the anatomical structure being automatically rotated and automatically translated from the first view to the second view.

3. The system according to claim 1, wherein the processor is configured to render the user interface screen presentation on the display showing the graphical representation of the anatomical structure being automatically rotated and automatically translated from the first view to the second view so as to center the selected feature in a panel of the user interface screen presentation.

4. The system according to claim 1, wherein the processor is configured to render the user interface screen presentation on the display showing the graphical representation of the anatomical structure being automatically rotated from the first view to the second view and automatically zoomed in at the second view to enlarge the selected feature.

5. The system according to claim 1, wherein the processor is configured to generate at least part of the feature list from medical readings performed by the medical device with respect to at least some of the plurality of features.

6. The system according to claim 5, wherein the medical readings include any one or more of the following: a location of a catheter; at least one location of at least one electrode of the catheter; a location where an Electrocardiogram (ECG) had been performed; a location where an ablation has been performed; or a location where the ablation is planned to be performed.

7. The system according to claim 6, further comprising a probe including the plurality of electrodes and being configured to perform the ablation.

8. The system according to claim 1, wherein the processor is configured to receive an input from the user interface indicating addition of an annotation to the graphical representation at a respective location, the processor being configured to add the annotation to the feature list.

9. The system according to claim 8, wherein the annotation forms a perimeter of a shape.

10. The system according to claim 9, wherein the processor is configured to render the user interface screen presentation on the display showing the graphical representation of the anatomical structure being automatically rotated and automatically translated from the first view to the second view so as to center the annotation based on a centroid of the shape of the annotation.

11. A method comprising:
   receiving a three-dimensional (3D) image of an anatomical structure in a body of a living subject;
   preparing a user interface screen presentation including a graphical representation of the anatomical structure based on the 3D image;
   generating a feature list of a plurality of features associated with the anatomical structure, each of the features having a respective location;
   rendering the user interface screen presentation to a display showing a first view of the graphical representation of the anatomical structure;
   while showing the first view, receiving an input from a user interface selecting a feature from the list; and
   rendering the user interface screen presentation to the display showing the graphical representation of the anatomical structure being automatically rotated from the first view to a second view showing the selected feature at the respective location on the graphical representation, including showing the anatomical structure as it is being rotated until the selected feature is shown.

12. The method according to claim 11, further comprising rendering the user interface screen presentation on the display showing the graphical representation of the anatomical structure being automatically rotated and automatically translated from the first view to the second view.

13. The method according to claim 11, further comprising rendering the user interface screen presentation on the display showing the graphical representation of the anatomical structure being automatically rotated and automatically translated from the first view to the second view so as to center the selected feature in a panel of the user interface screen presentation.

14. The method according to claim 11, further comprising rendering the user interface screen presentation on the display showing the graphical representation of the anatomical structure being automatically rotated from the first view to the second view and automatically zoomed in at the second view to enlarge the selected feature.

15. The method according to claim 11, wherein the generating includes generating at least part of the feature list from medical readings performed by a medical device with respect to at least some of the plurality of features.

16. The method according to claim 15, wherein the medical readings include any one or more of the following: a location of a catheter; at least one location of at least one electrode of the catheter; a location where an Electrocardiogram (ECG) had been performed; a location where an ablation has been performed; or a location where the ablation is planned to be performed.

17. The method according to claim 16, further comprising performing the ablation.

18. The method according to claim 11, further comprising: receiving an input from the user interface indicating addition of an annotation to the graphical representation at a respective location; and adding the annotation to the feature list.

19. The method according to claim 18, wherein the annotation forms a perimeter of a shape.

20. The method according to claim 19, further comprising rendering the user interface screen presentation on the display showing the graphical representation of the anatomical structure being automatically rotated and automatically translated from the first view to the second view so as to center the annotation based on a centroid of the shape of the annotation.

21. A system comprising:
a user interface comprising a display and an input device; and
a processor configured to:
prepare a user interface screen presentation including a graphical representation of an anatomical structure based on a three-dimensional (3D) image of the anatomical structure in a body of a living subject;
generate a feature list of a plurality of features associated with the anatomical structure, each of the features having a respective location;
render the user interface screen presentation to the display showing a first view of the graphical representation of the anatomical structure;
while showing the first view, receive an input from the user interface selecting a feature from the list; and
render the user interface screen presentation to the display showing the graphical representation of the anatomical structure being automatically rotated from the first view to a second view showing the selected feature at the respective location on the graphical representation, including showing the anatomical structure as it is being rotated until the selected feature is shown.

22. The system according to claim 21, wherein the processor is configured to render the user interface screen presentation on the display showing the graphical representation of the anatomical structure being automatically rotated and automatically translated from the first view to the second view.

23. The system according to claim 21, wherein the processor is configured to render the user interface screen presentation on the display showing the graphical representation of the anatomical structure being automatically rotated and automatically translated from the first view to the second view so as to center the selected feature in a panel of the user interface screen presentation.

24. The system according to claim 21, wherein the processor is configured to render the user interface screen presentation on the display showing the graphical representation of the anatomical structure being automatically rotated from the first view to the second view and automatically zoomed in at the second view to enlarge the selected feature.

25. The system according to claim 21, wherein the processor is configured to generate at least part of the feature list from medical readings performed by a medical device with respect to at least some of the plurality of features.

26. The system according to claim 25, wherein the medical readings include any one or more of the following: a location of a catheter; at least one location of at least one electrode of the catheter; a location where an Electrocardiogram (ECG) had been performed; a location where an ablation has been performed; or a location where the ablation is planned to be performed.

27. The system according to claim 21, wherein the processor is configured to receive an input from the user interface indicating addition of an annotation to the graphical representation at a respective location, the processor being configured to add the annotation to the feature list.

28. The system according to claim 27, wherein the annotation forms a perimeter of a shape.

29. The system according to claim 28, wherein the processor is configured to render the user interface screen presentation on the display showing the graphical representation of the anatomical structure being automatically rotated and automatically translated from the first view to the second view so as to center the annotation based on a centroid of the shape of the annotation.

30. A software product, comprising a non-transient computer-readable medium in which program instructions are stored, which instructions, when read by a central processing unit (CPU), cause the CPU to:
prepare a user interface screen presentation including a graphical representation of an anatomical structure based on a three-dimensional (3D) image of the anatomical structure in a body of a living subject;
generate a feature list of a plurality of features associated with the anatomical structure, each of the features having a respective location;
render the user interface screen presentation to a display showing a first view of the graphical representation of the anatomical structure;
while showing the first view, receive an input from a user interface selecting a feature from the list; and
render the user interface screen presentation to the display showing the graphical representation of the anatomical structure being automatically rotated from the first view to a second view showing the selected feature at the respective location on the graphical representation, including showing the anatomical structure as it is being rotated until the selected feature is shown.

\* \* \* \* \*